United States Patent
Elsner et al.

(10) Patent No.: US 6,262,256 B1
(45) Date of Patent: Jul. 17, 2001

(54) ARTICLE FOR TUESYL-ACTIVATED DEXTRAN FOR SOLID-PHASE COUPLING

(75) Inventors: Henrik Elsner, Brøinshøj; Søren Mouritsen, Birkerød, both of (DK)

(73) Assignee: Mouritsen & Elsner A/S, Copenhagen (DE)

( * ) Notice: Subject to any disclaimer, the term of this patent is extended or adjusted under 35 U.S.C. 154(b) by 0 days.

(21) Appl. No.: 09/073,646

(22) Filed: May 6, 1998

Related U.S. Application Data

(62) Division of application No. 08/379,675, filed as application No. PCT/DK93/00259 on Aug. 10, 1993, now Pat. No. 5,874,569.

(30) Foreign Application Priority Data

Aug. 10, 1992 (DK) .................................................. 1005/92

(51) Int. Cl.⁷ .................................................. C08B 37/02
(52) U.S. Cl. .............................. 536/112; 536/51; 525/54.2
(58) Field of Search ...................... 536/51, 112; 525/54.2

(56) References Cited

U.S. PATENT DOCUMENTS

| | | | |
|---|---|---|---|
| 4,066,509 | * | 1/1978 | Ceska ............................ 195/103.5 R |
| 4,111,751 | * | 9/1978 | Lange ................................. 195/66 R |
| 4,612,281 | | 9/1986 | Desmonts ................................. 435/7 |
| 4,744,760 | * | 5/1988 | Molday ..................................... 424/3 |
| 4,959,306 | | 9/1990 | Kameda et al. ........................... 435/7 |
| 4,975,532 | | 12/1990 | Rowley et al. ......................... 536/51 |
| 5,030,697 | | 7/1991 | Hugl ................................. 525/326.9 |
| 5,116,962 | | 5/1992 | Stuber et al. ........................... 525/54 |
| 5,139,881 | * | 8/1992 | Henis ................................... 424/488 |
| 5,198,493 | | 3/1993 | Holmberg ........................... 525/54.1 |
| 5,240,994 | | 8/1993 | Brink ................................. 525/54.2 |
| 5,242,828 | * | 9/1993 | Bergstrom ............................ 435/291 |
| 5,436,161 | * | 7/1995 | Bergstrom ............................ 435/291 |
| 5,492,840 | * | 2/1996 | Malmquist ............................ 436/518 |
| 5,516,673 | | 5/1996 | Margel ................................. 435/188 |
| 5,746,999 | * | 5/1998 | Gries ................................. 424/9.322 |

FOREIGN PATENT DOCUMENTS

| | | |
|---|---|---|
| 0 269 451 | 6/1988 | (EP) . |
| 90/06954 | 6/1990 | (WO) . |
| 91/05817 | 5/1991 | (WO) . |
| 91/09877 | 7/1991 | (WO) . |
| 92/03732 | 3/1992 | (WO) . |
| 92/07006 | 4/1992 | (WO) . |

OTHER PUBLICATIONS

Carruthers, Some Modern Methods of Organic Synthesis, pp. 348–350, 1978.
Groman, TIBTECH 5, 220, 1987.
Hermanson, Immobilized Affinity Ligand Techniques, 85–88, 144, 145, 214.
Nilsson, Meth Enzymol 135, 65–78, 1987.

* cited by examiner

*Primary Examiner*—Christopher S. F. Low
*Assistant Examiner*—D. Lukton
(74) *Attorney, Agent, or Firm*—Jacobson Holman PLLC

(57) ABSTRACT

A method of modifying the binding properties on a surface of a solid phase on which there are nucleophilic groups, which is characterized in that the surface is treated with a solution of an activated polysaccharide; a method of immobilizing a chemical compound to a solid phase on which there are immobilized activated polysaccharides, whereby the chemical compound is contacted with the surface of the solid phase the binding properties of which are modified by the method according to the invention; an article which is characterized in that to the surface thereof an activated polysaccharide is fixated, such as activated dextran or activated agarose, and use of this article for use in solid phase reactions, in solid phase assay, solid phase peptide synthesis, solid phase nucleotide synthesis, solid phase enzyme processing, and joining of biological surfaces.

2 Claims, 12 Drawing Sheets

ARTICLE FOR TUESYL-ACTIVATED DEXTRAN FOR SOLID-PHASE COUPLING

This is a division of application Ser. No. 08/379,675, filed Mar. 22, 1995 now U.S. Pat. No. 5,874,569, which application is a 371 of PCT/DK93/00259, filed Aug. 10, 1993.

The present invention relates to a method of modifying the binding properties of the surface of a solid phase on which nucleophilic groups are present, a method of immobilizing a chemical compound to the surface of a solid phase, and the solid phase modified by the method in the form of an article, and the use thereof in solid phase reactions.

THE TECHNICAL FIELD

Immobilization of various chemical compounds to surfaces of solid phases, such as glass and plastic materials or other solid materials, is used in a variety of chemical and biochemical techniques in which the chemical compound is bound to the surface of the solid phase, in order to be able at this locality to form part of solid phase reactions with other chemical compounds. Such solid phase reactions occur e.g. within chromatography, solid phase assays, including biosensors and solid phase peptide and oligonucleotide synthesis, and they are also used in bioreactors. Further, solid phase reactions occur e.g. in chemical surface treatment of biological surfaces, such as teeth, as a step in glueing items thereon.

Methods of immobilizing chemical compounds to solid phases are multifarious and depend on the object, but within the fields of application mentioned below the present invention constitutes a clear improvement over the existing techniques, since e.g. the durability of immobilized proteins is improved, the functionality is retained, and it is possible to recognize/immobilize peptides.

DESCRIPTION OF THE KNOWN ARE

Use of solid phase assay technique, including Enzyme Linked Immunosorbent Assays (ELISA) (Engvall E. and Perlmann P. "Enzyme-linked immunosorbent assay, ELISA. Quantitation of specific antibodies by enzyme-labeled anti-immunoglobulin in antigene-coated tubes", J. Immunol, 109: 129–35, 1972) and solid phase radioimmunoassays (RIA), has during recent years been growing strongly for concentration determination of both antigenes and antibodies. Furthermore solid phase assays and the appertaining radioactive or non-radioactive detection systems are used in gene probe based hybridization assays and in biosensors.

By conventional ELISA or solid phase-RIA-technique antigenes/antibodies are most often immobilized to the solid phase by passive adsorption. Certain proteins, peptides, polysaccharides, haptenes and oligo-/poly-nucleotides can, however, not be immobilized/detected in this way, and other compounds are denatured and destroyed in the adsorption process (Kurki P. and Virtanen I. "The detection of human antibodies against cytoskeletal components". J. Immunol. Methods, 67: 209–23, 1984).

Further, the orientation of the antigene after immobilization to the solid phase may in certain cases be such that some parts are sterically hindered against interaction with e.g. the antibody. Finally, there may in several cases be a number of serious problems of unspecific (and undesired) binding of the succeeding (maybe enzyme- or isotope-labeled) compounds in the ELISA-or RIA-methods.

Some of the problems can be overcome by methods where the micro-titre-plate is chemically modified with functional groups, whereafter non-adsorbing molecules can be bound covalently by conventional cross-linking technology (cf. e.g. Neurath, AR and Strick, N "Enzyme-linked fluorescence immunoassays using beta-galactosidase and antibodies covalently bound to polystyrene plates. J. Virol. Methods. 3: 155–65, 1981, and e.g. GlueTech Aps "A method for covalent fixation of molecules on a solid phase", WO89/05329).

Often, however, this does not solve the problems of denaturing and consequently deterioration of the quality of the immobilized oligo-/polypeptides or oligo-/poly-nucleotides, since the hydrophobic solid surface is still present. Furthermore, the technique requires quite some chemical expertise on the part of the performer, since use must be made of biofunctional cross-linking reagents. This is also so if the problem is sought solved by non-adsorbing molecules, such as e.g. peptides, being conjugated to larger proteins before the latter subsequently are adsorbed to the solid phase. In this case it is further necessary to use relatively large peptide quantities as compared with the present method.

Covalent immobilization of proteins, such as e.g. antibodies, is well-known in connection with affinity chromatography, where the molecules at issue are coupled to a solid phase consisting of a cross-linked, insoluble, activated, hydrophilic polymer, such as e.g. agarose or dextran (Pharmacia "Affinity chromatography. Principles & Methods", 1986). Such surfaces are capable of efficiently and covalently binding large quantities of molecules without the biological function or structure thereof being affected. Additionally, the numerous hydrophilic groups (e.g. ether and alcohol groups) in the said polymers cause the surface to be hydrophilic, whereby succeeding unintended adsorption of e.g. protein is avoided. In other words, the surface has "non-binder" properties, except as regards the covalent coupling of the protein, which takes place via its functional groups (e.g. amino groups). Cross-linked dextran and agarose thus have a number of expedient binding properties which as such would be well-suited in solid phase techniques, but the disadvantages of these materials are firstly that they cannot be shaped as e.g. micro-titre-plates, and secondly that they are totally opaque, which makes it impossible to use the material in assays in which optical detection methods are employed.

Published international patent application No. WO91/09877 discloses a method of covalent binding of a protein to a hydrophilic surface consisting of a non-ionic polymer exhibiting protein-reactive groups, by which a low spontaneous adsorption of undesired products is simultaneously obtained. According to the invention the non-ionic polymer which is bound to a carrier in a manner known per se must in order that the protein subsequently can be coupled effectively to the surface, also exhibit a "cloud-point" which lies at least 5° above the temperature at which the hydrophilic surface is to immobilize the protein. Hereby it is purportedly achieved that the non-ionic immobilized polymer at an elevated temperature becomes more willing to establish the binding to the protein. Binding to anionic surfaces is specifically described.

Published international patent application WO90/06954 describes monoclonal antibodies which recognize poly-sulphated polysaccharides. Coating of activated polyvinyl chloride-immunoassay plates with poly-L-lysine to which dextran sulphate is bound by an ionic binding is specifically described.

Both synthetic oligonucleotides and peptides are today typically prepared by solid phase chemical synthesis on so-called resins (cf. e.g. E. Atherton and R. C. Sheppard "Solid-phase peptide synthesis: A practical approach", IRL Press). Frequently used resins for peptide synthesis consist of diatomaceous earth grafted with polyacrylamide, but they may also consist of cross-linked polystyrene (Merrifield's resin) (see e.g. E. Atherton and R. C. Sheppard "The solid phase in solid phase peptide synthesis", in "Perspectives in Peptide Chemistry", Eds. E. Eberle, R. Geiger, and T. Wieland, 1981, p. 101). It has, however, turned out to be an advantage synthesis-wise that the resin has hydrophilic properties like e.g. the PEG-resin which consists of a copolymer of polystyrene and polyethylene glycol (PEG) (see e.g. Jiang, Ying; Liang, Xun; Chen, Weizhu; He, Binglin "Synthesis of polystyrene-supported polyethylene glycol and study of its property in peptide synthesis", Huaxue Xuebao, 45(11), 1112–18).

Technically, peptide synthesis can be performed on amino group modified, insoluble, cross-linked agarose or dextran, since such surfaces will also be hydrophilic. For mechanical reasons these materials are, however, not suited for this purpose, since they are compressible and fragile. Besides, the flow and swelling properties in organic solvents, such as DMF, are poor. Consequently, it would be expedient to have a technique which combines the advantages of the existing resins with the hydrophilic properties of e.g. dextran.

For industrial applications use is frequently made of immobilization of various enzymes. An example is treatment of non-fermentable carbohydrates in beer with immobilized amyloglycosidase in view of producing fermentable carbohydrates. When immobilizing the enzymes it is important that they retain their biological activity. Immobilization of enzymes can therefore successfully be made on cross-linked agarose or dextran. The abovementioned unfortunate mechanical properties of these materials, however, make them unsuited for this, since cross-linked dextran or agarose is compressed at relatively low superpressures.

Consequently, there exists a need to be able to provide desired binding properties on the surface of solid phases which are mechanically stable, optionally transparent, and to which all types of molecules can be immobilized without getting denatured or having their functionality impaired.

DESCRIPTION OF THE INVENTION

It is an object of the present invention to provide a method of modifying the binding properties of the surface of a solid phase on which nucleophilic groups are present, whereby molecules, such as oligo-/polypeptides, oligo-/polysaccharides or polynucleotides can be bound covalently. It is furthermore the object that the surface at the same time obtains poor unspecific binding properties (non-binder properties).

It is also an object of the present invention to provide a method of immobilizing biomolecules to the surface of such a solid phase without the structure and function of the biomolecule thereby being destroyed.

Finally, it is an object of the present invention to provide solid phases in the form of articles for use in solid phase reactions, such as solid phase assays or solid phase synthesis.

It has surprisingly been found that when activated polysaccharide, such as activated dextran or activated agarose, is bound covalently to the surface of a solid phase on which nucleophilic groups, such as $NH_2$- and SH-groups, are present, new surfaces are obtained having the properties described above.

The above objects are consequently achieved by providing a method of modifying the binding properties of a surface of a solid phase on which there are nucleophilic groups, which method is characterized by the features stated in the characterizing portion of claim 1.

By the method according to the invention solid phases are obtained, the surfaces of which possess improved capacity for reacting with chemical compounds of relevant kind, and in several cases possess improved capacity for binding such compounds with an improved durability.

Further it is possible to achieve functional, transparent surfaces which can readily be used in solid phase assays, where e.g. micro-titre-plates or strips constitute the solid phase. According to the invention use is made of an activated polysaccharide which is not a cellulose ether, and which does not have a "cloud-point", and which acts as a kind of multifunctional cross-linking reagent which connects e.g. antigenes or antibodies to the solid phase, the polysaccharide being activated in such a way that the activated groups can form covalent bonds.

Examples of such polysaccharides are activated dextran and activated agarose. Instead of dextran and agarose use can be made of corresponding amounts of other polymers containing OH-groups, such as other natural or synthetic poly- or oligosaccharides, e.g. gum xanthan or polyalcohols, such as polyvinyl alcohol or polyhydroxy methyl methacrylate.

A micro-titre-plate containing primary amino groups may e.g. be treated with periodate or tresyl-activated dextran or agarose, whereby the surface obtains quite new and strongly improved binding properties.

It should be noted that the well-known problem of making e.g. proteins bind covalently to solid phases (WO 91/09877) can on the surface according to the present invention be overcome by including in the binding process polyethylene glycol in the solution.

The surprising advantages of the invention are thus that a micro-titre-plate in a particularly simple way can be imparted with the expedient physicochemical properties which are e.g. known from materials used for affinity chromatography. Here the excess hydrophilic groups (e.g. ether- and alcohol-groups) in the said polymers cause the surface to be hydrophilic and in other words possessing the same non-binder properties. It is further achieved that the function and structure of the biomolecules are retained after binding to the surface. Hereinafter the method is designated "hydro-coating".

By the method according to the invention it is possible by coupling of resins for e.g. peptide synthesis with activated dextran to further improve its hydrophilic properties, whereby it is possible to achieve a more efficient peptide synthesis. Similar improvements can be expected by using such modified resins in solid phase oligonucleotide synthesis.

In a certain application of synthetic peptides—the so-called arbitrary synthetic peptide libraries—the thus added hydrophilic non-binder properties of the resin balls are of particularly high importance (see Lam K S; Salmon S E; Hersh E M; Hruby V J; Kazmierski W M; Knapp R J "A new type of synthetic peptide library for identifying ligand-binding activity", Nature, 354, 82–4).

The following examples demonstrate that hydro-coated surfaces retain the quality of immobilized biomolecules. Consequently, it must be expected that probably hydro-coating can improve certain of the "solid phase" materials which are used for e.g. "solid phase" enzyme processing, as mentioned above. At the same time the known expedient mechanical properties of these materials are retained.

A technique for glueing on e.g. broken tooth stumps, ceramic fillings etc, is described by Munksgaard, E. C. and Asmussen, E. "Dentin-polymer bond mediated by glutaraldehyde/HEMA", Scand. J. Dent. Res., 93(5), 463–6, 1985. Here the tooth surface is first treated with hydrofluoric acid, whereby the amino groups in the dentin are exposed. Next treatment is with glutaraldehyde and methylmethacrylate, whereafter polymerization of the latter is initiated with UV-light. Hereby the tooth stump or the ceramic filling is thus glued on with polymethacrylate, and the covalent connection to the amino groups is established with the cross-linking reagent glutaraldehyde.

However, glutaraldehyde is associated with a number of working environmental disadvantages. Additionally, it is often seen that the methacrylate-monomer, which is toxic, does not diffuse into the patient. Alternatively it is therefore suggested that periodate-activated dextran is used for pre-treating the hydrofluoric acid treated dentin surface. Hereby a coating is performed with a well-known biocompatible material, and it must be expected that the aldehyde groups on the dextran will have the same initiating effect as glutaraldehyde on the succeeding methylmethacrylate-polymerization. It is further to be expected that the hydrophilic dextran layer will effectively prevent the hydrophobic methylmethacrylate-monomers from penetrating into the patient. Thus it is demonstrated that apparently hydro-coated surfaces can prevent N-hydroxy-succinimide-biotin from penetrating through the carbohydrate layer (example 11).

Preferred embodiments are stated in the claims.

BRIEF EXPLANATION OF THE FIGURES

In the following the invention is explained in more detail, reference being made to the drawings in which.

DETAILED DESCRIPTION OF THE INVENTION

Figure 1:
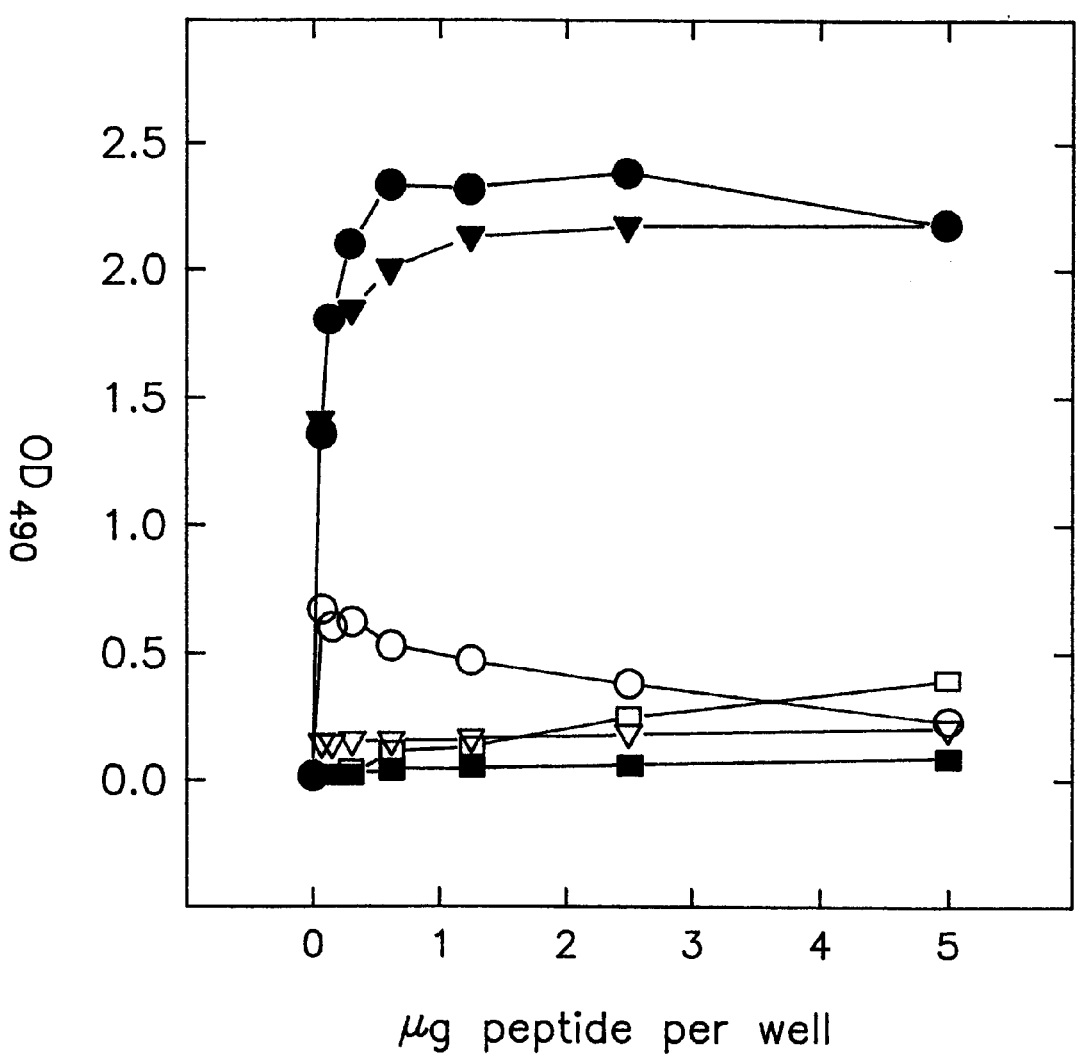
FIG. 1 shows binding of biotin-MP7 to micro-titre-plates with (●) and without POD (○), respectively; binding of biotin-MP9 to micro-titre-plates with (▼) and without POD (▽), respectively, and binding of biotin-peptide T to micro-titre-plates with (■) and without POD (□), respectively.

In short, the principle of "hydro-coating" is to couple a solid phase with an activated polysaccharide which hereby will act as a kind of "double adhering" tape.

By the technique it is possible to immobilize molecules which do not normally adsorb to conventional micro-titre-plates. It may be a case of peptides, haptenes, double-stranded DNA, oligonucleotides etc, which enables e.g. measurement of antibodies to these components. This object of the present invention is illustrated in examples 3, 4 and 9.

It is further demonstrated that the destruction of the structure and function of biomolecules, which some times can be seen by passive adsorption to plastics, does not take place when coupling to hydro-coated surfaces. The quality of the coupled biomolecules is in other words better. This is illustrated in examples 3, 4, 5, 7 and 8. The presence of PEG during the coupling considerably improves it, which is illustrated in example 6.

Finally, it is demonstrated that the capacity of hydro-coated surfaces for covalent binding can be eliminated in a simple way, whereby the surface is converted to an especially efficient non-binder. This is shown in example 12. This surface is thus also rejecting towards membrane molecules which otherwise bind unspecifically to conventional micro-titre-plates—even in spite of the presence of detergent.

Usually it is necessary to have nucleophilic groups on the surface of the solid phase which it is desired to treat by the method according to the invention. This is achievable in various ways. Several micro-titre-plates are already on the market, where e.g. primary or secondary amino groups are associated covalently to the surface of the plate (e.g CovaLink from A/S Nunc, Denmark, or Costar, USA).

Alternatively, coating can merely be by passive adsorption to the solid phase with e.g. protein, polyamine or poly-L-lysine, whereby amino groups are introduced non-covalently on the surface. It is well-known that this lastmentioned method leads to an especially stable modification, even through covalent forces are not involved. Other polymers containing the mentioned functional groups are similarly adsorbable to the surface, just as such groups can be introduced by various chemical methods (see e.g. "Radiation grafting", EP-A-155 252).

In the examples shown dextran is used as the polysaccharide. However, also other oligo- or polysaccharides, such as e.g. agarose, are usable.

In most of the examples shown use is made of perjodate-activated dextran, but examples are also shown where the dextran has been supplied with tresyl-groups. This is possible since it has surprisingly been found that dextran is soluble in the aprotic solvent hexamethyl phosphorous triamide (HMPTA) or N-methyl-pyrrolidinone, where a specific reaction between tresyl chloride and dextran can take place. It is also possible to dissolve dextran in dimethyl sulfoxide (DMSO), but this makes the succeeding reaction with tresyl chloride impossible, since DMSO reacts with sulphonic acid chlorides.

It is also possible to introduce other active groups in dextran, whereby the plate in some cases will even be more selective in its binding of biomolecules. On the hydrophilic polymer introduction may e.g. be made of aldehydes, ketones, vinyl sulphones, cyanogens, active esters, epoxides, disulfides and other active compounds of carboxylic acid, phosphoric acid and sulphonic acid. The mentioned activated groups can e.g. be attached separated by a "spacer-arm", whereby any sterical problems can be further alleviated.

EXAMPLES

Example 1

Modification of the binding properties of a polystyrene surface by pretreatment thereof with poly-L-lysine and succeeding fixation of periodate-activated dextran
(a) Preparation of periodate-activated dextran (POD)

Dextran (100 mg, molecular weight (MW)=70,000 Sigma D4751) was dissolved in 50 ml of water, followed by addition of sodium periodate (398 mg, 3.3 mmole Aldrich 311448). After stirring for 2 hours dialysis was performed 3 times with 5 l pure water.

Instead of dextran use is made of corresponding amounts of agarose or other natural or synthetic oligo- or polysaccharides, such as gum xanthan (Sigma, G 1253), or polyalcohols, such as polyvinyl alcohol or polyhydroxy methyl methacrylate.
(b) Fixation of POD to micro-titre-plates.

To a polystyrene-micro-titre-plate (Maxisorp, Nunc) addition was made to each well of poly-L-lysine (Sigma P1274, 50 μg) in carbonate buffer (0.1 M, pH 9.6), which was incubated for two hours. Hereafter the wells were washed 3 times with water. Then 100 μl of POD-solution was added to each well (50 μg in 100 μl PBS, pH 7.2, 0.1 M) which were left to stand for two hours, whereafter they were washed again 3 times with water.

The micro-titre-plate used did not in advance contain primary amino groups and was therefore pretreated with poly-L-lysine. This pretreatment has also been made with other polyamino acids containing primary amino groups, such as polypeptides, just as it has been made with polyamines, such as polimine on micro-titre-plates, micro-titre-strips, particles, membranes, test tubes, test strips or measuring pins consisting of materials, such as polyethylene glycol terephthalate, polyvinyl acetate, polyvinyl chloride, polyvinyl pyrrolidone, polyacrylonitrile and polymethacrylate.

It is known to introduce primary amino groups covalently on the surface of micro-titre-plates, and there are already polystyrene-micro-titre-plates on the market which have such amino groups on the surface (e.g. Costar, U.S.A.).

All the mentioned surfaces are treatable with POD as described above.

Example 2

Modification of the binding properties of a polystyrene surface by pretreatment thereof with poly-L-lysine and subsequent fixation of tresyl-activated dextran
(a) Production of tresyl-activated dextran (TAD)

Dextran (100 mg MW: 70,000, Sigma D4751) was dissolved in water (10 ml) and was freeze-dried overnight to reduce the content of free water. The next day the dextran (10 mg) was dissolved in HMPTA (20 ml, Sigma H4006) at 120° C. in a 100 ml round-bottomed flask attached to a calcium-chloride tube with sicapent. After cooling freshly distilled pyridine (198 mg, 10.9 mmole, Aldrich 270407) and tresyl chloride (858 mg, 10.9. mmole, Aldrich 324787) were added. After two hours the dextran was precipitated with ethanol. Re-dissolution was in water, and again precipitation was with ethanol. Hereafter the active dextran was freeze-dried overnight.

Instead of dextran use is made of corresponding amounts of other polymers containing OH-groups, such as other natural or synthetic poly- or oligosaccharides, such as agarose or gum xanthan, or polyalcohols, such as polyvinyl alcohol or polyhydroxy methyl methacrylate.
(b) Fixation of TAD to micro-titre-plates To a polystyrene-micro-titre-plate (Maxisorp, Nunc) addition was made to each well of poly-L-lysine (50 μg) in carbon buffer (100 ml, 0.1 M, pH=9.6) which thereafter was incubated for two hours at room temperature. Then wash was performed 3 times with water. Thereafter 100 μl of TAD-solution was added to each well (50 μg in 100 μl PBS 0.1 M) and incubation was for additionally 2 hours, followed by wash 3 times with water.

The micro-titre-plate used had in advance neither primary or secondary amino groups and was therefore pretreated with poly-L-lysine. This pretreatment has also been performed with other polyamino acids and polypeptides containing primary and/or secondary amino groups, just as it has been performed with polyamines, such as polimine, on micro-titre-plates, micro-titre-strips, particles, plates, test tubes, test strips or measuring pins, consisting of materials, such as polyethylene glycol terephthalate, polyvinyl acetate, polyvinyl chloride, polyvinyl pyrrolidone, polyacrylonitrile and polymethacrylate.

Primary or secondary amino groups have also been introduced covalently in various ways, and polystyrene micro-titre-plates are already on the market which have such amino groups on the surface (e.g. Costar, USA, which contains primary amino groups, or CovaLink, Nunc, Denmark, which contains secondary amino groups).

All the mentioned surfaces are treatable with TAD as described above.

Example 3

Immobilization of peptides to a polystyrene surface with fixated periodate-activated dextran (a) Preparation of periodate-activated dextran (POD) Procedure as described in example 1.

(b) Fixation of POD to micro-titre-plates

To a polystyrene-micro-titre-plate (Maxisorp, Nunc) addition was made to each well in rows 1–6 of poly-L-lysine (100 µl, 50 µg) in carbonate buffer (0.1 M, pH 9.6) which were incubated for two hours. Hereafter wash was performed three times with water. Then 100 µl of POD-solution was added to each well in rows 1–12 (50 µg in 100 µl PBS, pH 7.1, 0.1 M), which stood for two hours followed again by wash 3 times with water.

(c) Immobilization of peptides to POD-fixated micro-titre-plates

The peptides biotin-MP7, biotin-MP9, and biotin-peptide-T, were titrated 2-fold in double determination in 7 steps starting with a concentration of 100 µg/ml in phosphate buffered saline water (PBS, 0.1 M, 100 µl/well) and ending with a concentration of 1.6 µg/ml. The peptides were titrated in double determination both in that half of the micro-titre-plate which was coated with poly-L-lysine and in that half which was not. After 2 hours the wells were emptied by suction and washed three times with washing buffer (NaCl 29.2 g, KCl 0.2 g, $KH_2PO_4H_2O$, Triton X-100 100 ml, distilled water to 1000 ml).

The peptides biotin-MP7 (biotin-PELFEALQKLFKHAY), biotin-MP9 (biotin-FAQKEPAFLKEYHLL), and biotin-peptide-T (biotin-GGGASTTNYT) were synthesized from Fmoc amino acid Pfp esters on a fully automated peptide synthesis machine (NovaSyn, Crystal) and thereafter purified by preparative HPLC. As the last step in the peptide synthesis biotin was coupled on in the form of an N-hydroxy-succinimide ester (Sigma).

(d) Detection of the immobilized peptides with and without biotin

Then 100 µl of avidin-peroxidase (25 µl avidin-peroxidase (DAKO), 100 mg of bovine serum albumin (BSA, Sigma), 10 ml of washing buffer) were added, whereafter the plates were incubated at room temperature for 1 hour. Hereafter the plates were washed again 3 times with washing buffer, and 100 µl of substrate was added per well (1 µl/ml 35% $H_2O_2$ and 1 mg o-phenylenediamine (OPD) per ml citrate/phosphate buffer (citric acid 7.3 g, $Na_2HPO_4$ H2O 11,86 g, distilled water to 1 l)). The colour reaction was stopped after 1–3 min. with 100 µl of $H_2SO_4$ (1 M), and the adsorbance (optical density, OD) was read on a Dynatech ELISA-reader.

Result and Discussion

It is seen from FIG. 1 that biotin-MP7 and -MP9 could be detected on a POD-treated micro-titre-plate. Biotin-peptide-T, however, could not. Further, no or only vague binding/detection could be seen of biotin-MP7/MP9 to a micro-titre-plate without addition of poly-L-lysine in spite of addition of POD.

Biotin-MP7/MP9 contain lysines and consequently free primary amino groups. This, however, is not so for biotin-peptide-T, which does not contain lysine. Thus the result shows that binding of the peptides to POD-treated surfaces is due to a specific covalent binding to the excess aldehyde- and ketone-groups on the POD-surface. If the surface does not contain amines, POD 70,000 does not bind, and consequently the peptides can only to a low degree or not at all be detected on the surface. However, if very high-molecular POD (MW>1 000 000) is used, POD can, however, to a low degree be bound to the plastic surface without preceeding introduction of amino groups thereon (data not shown). Presumably, this is, however, due to passive adsorption of POD to the surface.

Aldehydes and ketones are capable of forming stable bonds (imines) with primary but not with secondary or tertiary amines. Other experiments have demonstrated that it is not possible to bind POD and thereby peptides to surfaces containing secondary amino groups (Covalink micro-titre-plates, data not shown). This further substantiates that immobilization of biotin-MP7/MP9 is due to a chemical cross-linking between primary amino groups on the poly-L-lysine surface and on the peptide and the carbonyl groups on POD, respectively.

On an untreated micro-titre-surface either an extremely poor or no signal at all was seen for all the peptides. This is either because: a) that the peptide does not bind or: b) that the adsorption of the peptide to the micro-titre-plate prevents avidin from reacting with biotin. We have demonstrated in other experiments that MP7 apparently binds to plates which are not treated with POD. Thus, we have immoblized non-biotinylated MP7, as described above, partly to POD, and partly to untreated surfaces. These were hereafter incubated with the monoclonal anti-MP7 antibody, MP7.4, and thereafter with peroxidase-labeled rabbit anti-mouse Ig. Here again a strong signal was seen on the plate treated with POD—even when coating was only with 0.050 µg MP7 per well. If a micro-titre-plate was used which had been quite freshly coated with MP7, it was also possible to detect bound MP7 to the surface with MP7.4, if it was coated with at least 10 µg/well. This signal disappears, however, after few days, which indicates that MP7 slowly changes conformation in such a way that it cannot bind the MP7.4 antibody (data not shown). The signal on the POD plate remained, however, completely unchanged for the entire test period (weeks).

This example substantiates the fact that POD treated surfaces retain the structure and accessibility of the peptides, so that they can be recognized by antibodies or streptavidin. Furthermore, it is only necessary to use very small quantities of peptide when immobilizing to the POD surface as compared with the quantities which are necessary when using a conventional micro-titre-plate.

Example 4

Binding of peptides via tresyl-activated dextran (a) Preparation of tresyl-activated dextran (TAD)

Procedure as described in example 2.

(b) Fixation of TAD to micro-titre-plates

To a micro-titre-plate (Maxisorp, Nunc) addition was made to each well in rows 1–6 of poly-L-lysine (50 µg) in carbonate buffer (100 µl, 0.1 M, pH 0.6) which stood for two hours. Hereafter wash was performed 3 times with water. Then 100 µl of TAD was added to each well in rows 1–12 (50 µg in 100 µl of PBS 0.1 M) which stood for two hours, followed by wash 3 times with water.

(d) Immobilization and detection of peptides on TAD treated surfaces

Biotin-MP7, biotin-MP9, and biotin-peptide-T, were added to surfaces both with and without poly-L-lysine, and any immobilization thereof was detected as described in example 3.

Result and Discussion

Figure 2:
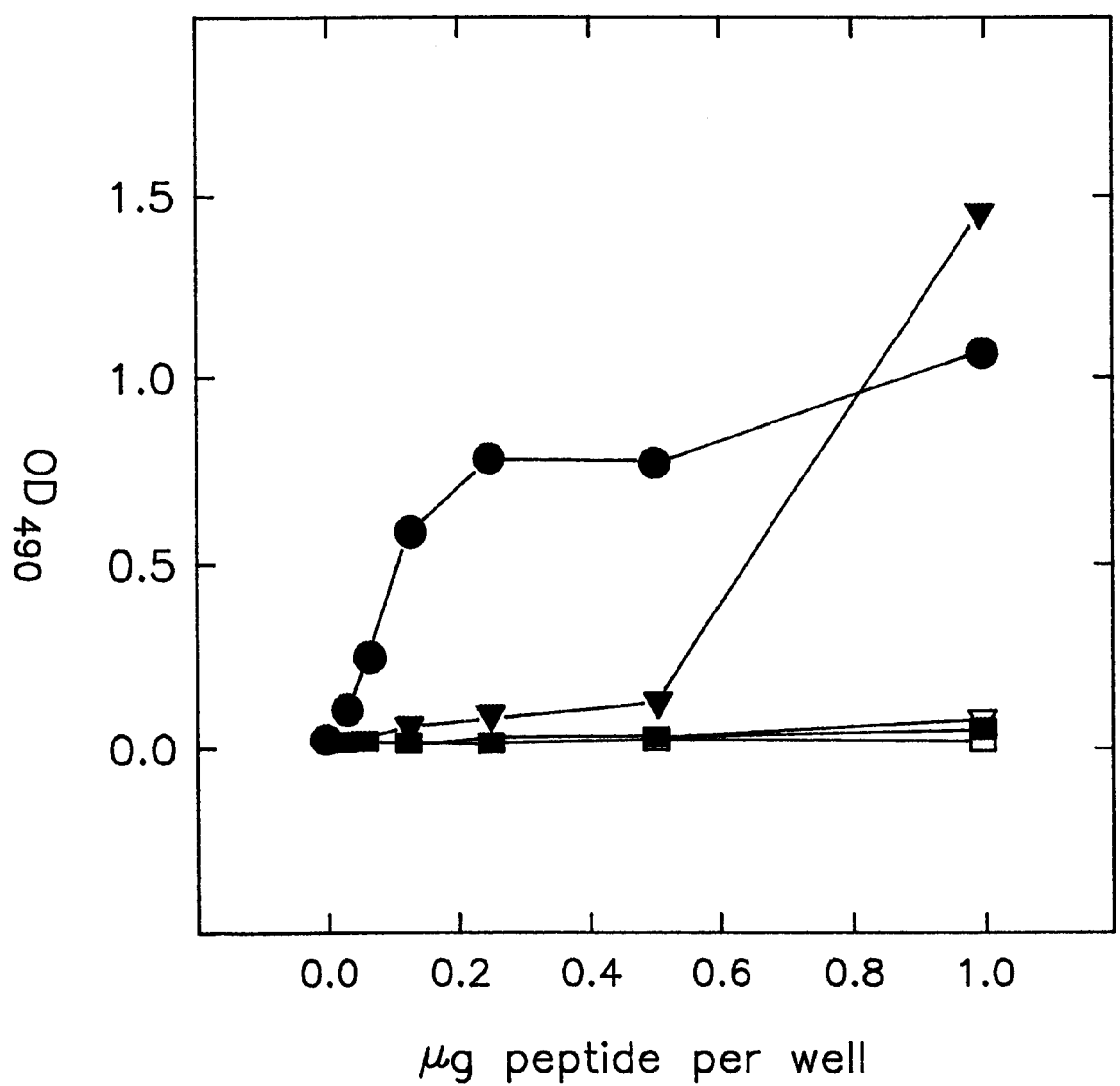
FIG. 2 shows binding of biotin-MP7 to micro-titre-plates with (●) and without TAD (○), respectively; binding of biotin-MP9 to micro-titre-plates with (▼) and without TAD (□), respectively, and binding of biotin-peptide T to micro-titre-plates with (■) and without TAD (□), respectively.

From FIG. 2 it is seen that biotin-MP7/MP9 bound strongly to TAD treated surfaces, but no binding of biotin-peptide-T was seen. Nor was any or only vague binding of the peptides to the surface seen without poly-L-lysine. Since biotin-MP7/MP9, but not biotin-peptide-T, contains free $NH_2$-groups, it can be concluded that the binding of peptide is due to a covalent immobilization via the tresyl-groups on the dextran. Tresyl-groups can, as opposed to aldehydes and ketones, form stable bonds with secondary amines. Thus we have also demonstrated that it is possible to treat the so-called CovaLink micro-titre-plates which contain secondary amino groups (A/S Nunc, Denmark), with TAD, but not with POD (data not shown). This substantiates that the peptide immobilization is due to a specific covalent binding. TAD additionally has the advantage that any excess tresyl-groups on the TAD-treated surface can be hydrolyzed off with base, whereby hydrophilic OH-groups are reestablished on the surface of the micro-titre-plate. Hereby the surface obtains non-binder properties as described in example 12. These OH-groups can optionally be further activated with e.g. cyanogen bromide or tresyl chloride in e.g. hexane, without the optical properties of the micro-titre-plates thereby being destroyed (data not shown). TAD treated surfaces further possess the same properties as POD treated surfaces as regards the useful effect on binding and structure preservation of the peptides, which was described in example 3.

Example 5

Immobilization of Immunoglobulin

Use was made of a micro-titre-plate where some wells had been treated with POD and others not, as described in example 3.

(a) Immobilization of peroxidase-labeled porcine immunoglobulin (PMS)

On a micro-titre-plate treated with POD, as described in example 3, a 2-fold titration was performed in double determination in 11 steps of PMS (DAKO) in PBS added with 15% PEG 4000 (polyethylene glycol with MW 4000) (100 µl/well). The same titration in double determination was also performed in wells without POD treatment, but in PBS without PEG. After 2 hours the wells were emptied by suction and washed three times with washing buffer.

(b) Detection of Immobilized PMS

This was performed with OPD as described in example 3.

Result and Discussion

Figure 3:
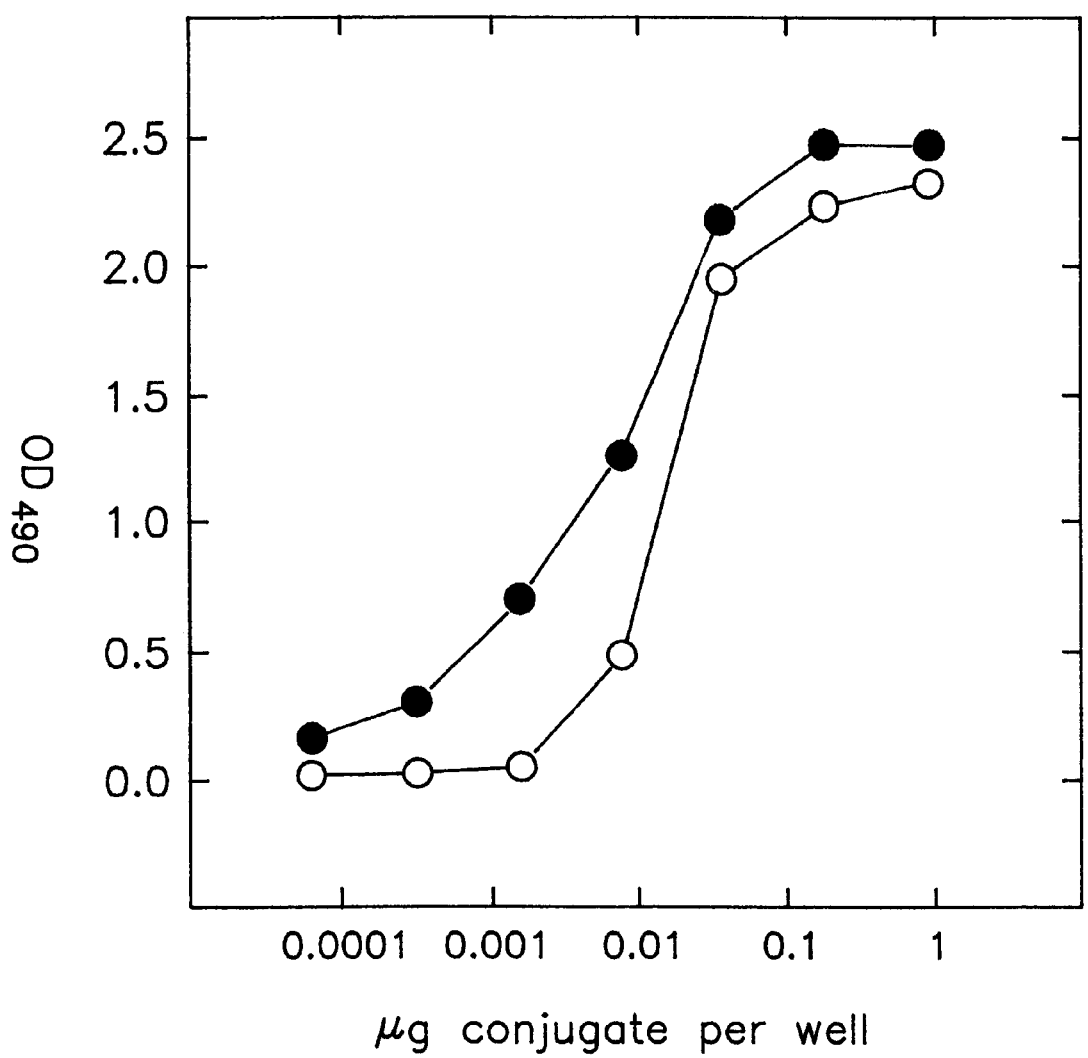
FIG. 3 shows the binding of peroxidase-labeled porcine immunoglobulin (PMS) to micro-titre-plate surfaces, which were and were not, respectively, coupled with POD. PMS added to a POD treated surface (●); PMS added to an untreated surface (○).

It is seen from FIG. 3 that generally relatively more porcine globulin can be immobilized/detected on the POD treated surface as compared with the optimal method of doing this on the untreated surface. This is still markedly in the low concentration area, where approx. 10 times as much PMS is immobilized/detected. It is well-known that perioxidase with time—because of denaturing—looses its enzymatic activity by passive adsorption to a plastic surface, and that this phenomenon gets more pronounced after a prolonged incubation period. The difference shown may thus be due to the POD-treated surface to a larger extent retaining peroxidase activity. It is likely that this will become more pronounced after prolonged incubation. PEG addition under immobilization of PMS to conventional micro-titre-plates impairs the result (data not shown), whereas quite the opposite is the case when immobilizing to POD (and TAD) treated surfaces (see example 4). This underlines the fundamentally different mechanisms on which the two methods are based.

Example 6

PEG's influence on the binding of Immunoglobulin

A micro-titre-plate was used where the wells had been treated with POD, as described in example 3.

(a) Immobilization of peroxidase-labeled porcine Immunoglobulin (PMS).

12 tubes were each added with 500 µl of PBS. In 11 thereof a titration of PEG 4000 from 30% to 0.02% was prepared, whereafter PMS (5 µg in 5 Ml) was added to each of the 12 tubes. Hereafter 100 µl of each solution were added to each separate well in double determination. After 2 hours the wells were emptied by suction, and they were washed three times with washing buffer.

(b) Detection of Immobilized PMS

This was done with OPD as described in example 3.

Result and Discussion

Figure 4:
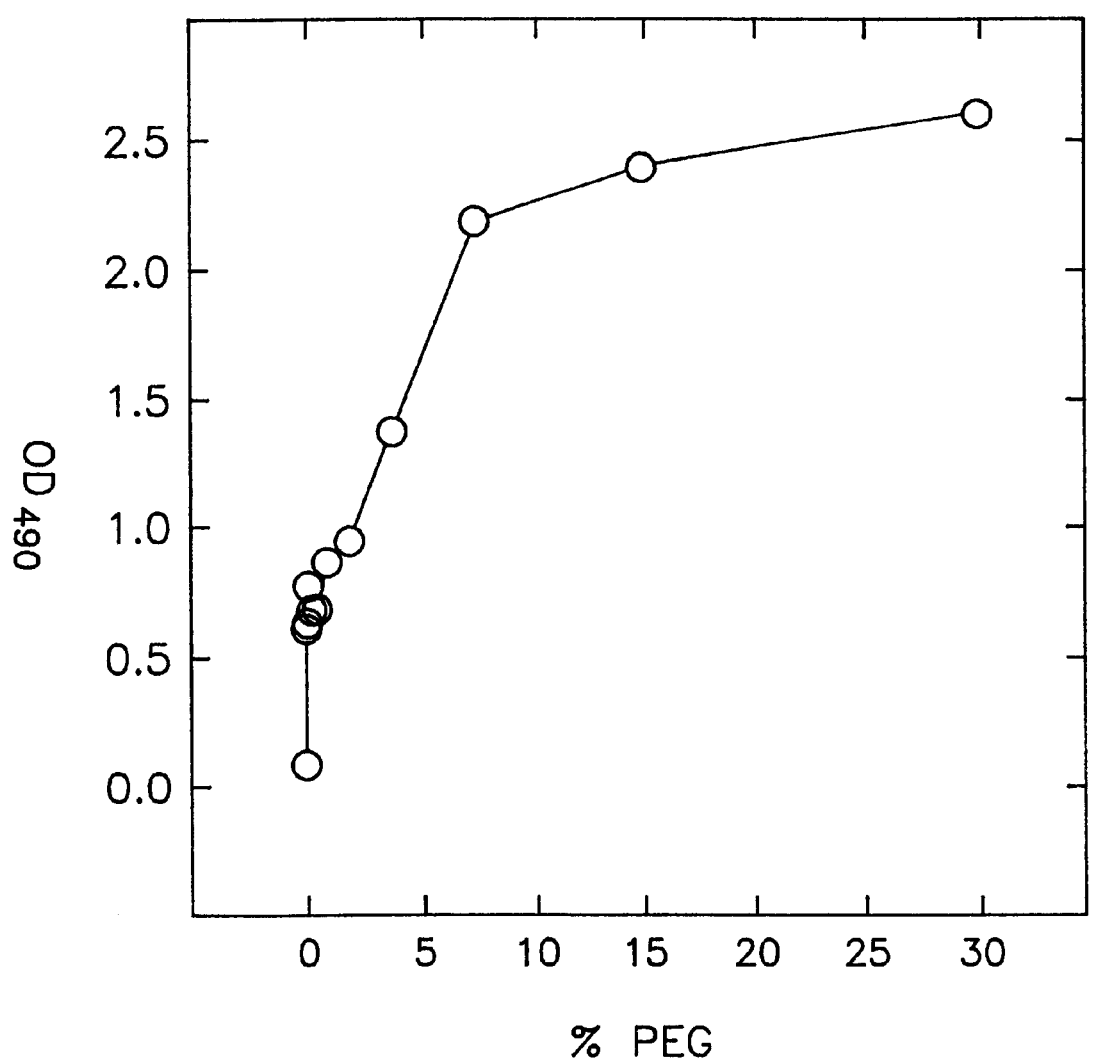
FIG. 4 shows the dependence on PEG when binding peroxidase-labeled porcine immunoglobulin to POD-treated surfaces.

From FIG. 4 it is seen that the detection of PMS drops significantly by use of less than 10% PEG. It is also well-known that PET improves coupling of proteins to e.g. vinyl sulphone activated sepharose. Most likely it is the same mechanism which lies behind this observation. The passive adsorption of protein to the micro-titre-plate on the contrary gets impaired if PEG is present (data not shown). PEG 4000 can be used (and is optimal for immobilizing the peptide biotin-MP7), but also other values of PEG have been found to function in our method.

This can be optimized depending on the nature of the compound to be immobilized.

Example 7

Use of hydro-coating in a sandwich-ELISA for concentration determination of mouse-immunoglobulin Use was made of a micro-titre-plate where rows 1 & 2 were treated with POD, and rows 3 & 4 were not, as described in example 3.

(a) Immobilization of Goat Anti-mouse Immunoglobulin (Ig)

100 µl of goat anti-mouse Ig (TAGO) (0.2 µg, 0.3 M carbonate buffer with 15% PEG 4000) were added to the wells in rows 1 and 2, and to rows 3 and 4 100 µl of goat anti-mouse Ig (0.2 µg, 0.3 M carbonate buffer). Hereafter incubation was for 2 hours at room temperature, followed by wash 3 times with water. Excess sites on the micro-titre-plate were then blocked with BSA (100 µl, 10 mg/ml in carbonate buffer). After 1 hour wash was performed 3 times with washing buffer).

(b) Addition of OX-6

The monoclonal mouse antibody, OX-6, was titrated 2-fold in all wells from 1 mg/ml in PBS, 100 µl/well. After incubation for additionally 1 hour wash was performed 3 times with washing buffer.

(c) Detection of Immobilized OX-6

Peroxidase-labeled rabbit anti-mouse Ig (DAKO) (1:1000, 100 mg BSA, 10 ml washing buffer) was added to all wells, followed by incubation for 1 our at room temperature. Thereafter the plates were washed 3 times with washing buffer, and the presence of immobilized peroxidase was detected as described in example 3.

Result and Discussion

Figure 5:
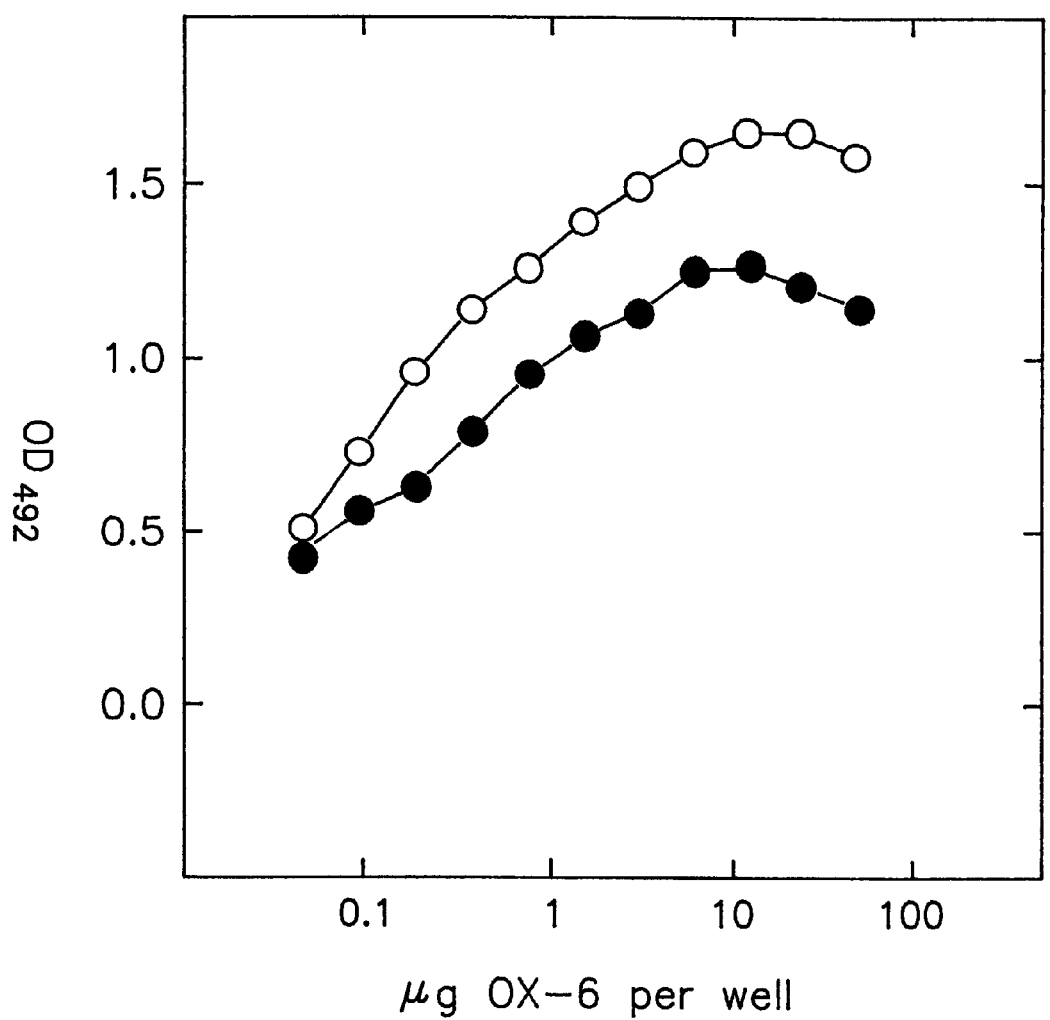
FIG. 5 shows the result of a sandwich-ELISA for concentration determination of murine immunoglobulin, where the catching antibody (goat anti-mouse immunoglobulin) was immobilized to a POD-treated surface (○) and an untreated micro-titre-plate surface (●), respectively. The accuracy of the assay was examined by titrating the intermediate layer which contained murine IgG (Ox6) and at the same time retaining the amount of the catching antibody.

A higher and steeper linear curve was seen when the catching antibody (goat anti-mouse Ig) was immobilized to a POD treated surface as compared with an untreated surface (FIG. 5). The precision and probably also the sensitivity of the assay was in other words better on a POD surface. This indicates that the quality of the catching antibody by covalent immobilization to hydrophilic POD surfaces is better than by passive adsorption. It cannot be left out, however, that this difference is due to the POD surface binding more catching antibody than the untreated surface.

Example 8

Binding of mouse-immunoglobulin to surfaces with varying amounts of goat anti-mouse Ig Use was made of a micro-titre-plate where rows 1 and 2 had been treated with POD, and rows 3 & 4 not, as described in example 3.

(a) Immobilization of Varying Amounts of Goat Anti-mouse Ig

100 µl of 0.3 M carbonate buffer with 15% PEG 4000 were added to rows 1 and 2, and 100 µl of 0.3 M carbonate buffer to rows 3 and 4. Then 100 µl of goat anti-mouse Ig (10 µg, 0.3 M carbonate buffer with 15% PEG 4000) were added to well 1A and 2A, and 100 µl of goat anti-mouse Ig (10 µg, 0.3 M carbonate buffer) to well 3A and 4A. Hereafter a 2fold titration in double determination was performed 5 times in carbonate buffer with and without PEG. Hereafter incubation was for 2 hours at room temperature, followed by blocking with BSA (100 µl, 10 mg/ml in carbonate buffer). After 1 hour w ash was performed 3 times with washing buffer.

(b) Addition of OX-6

To all wells in the four rows with goat anti-mouse Ig, 100 µl of OX-6 (1 µg, 100 µl PBS) were added. After 1 hour at room temperature wash was performed with washing buffer.

(c) Detection of immobilized OX-6

This was done as described in example 7.

Result and Discussion

Figure 6:
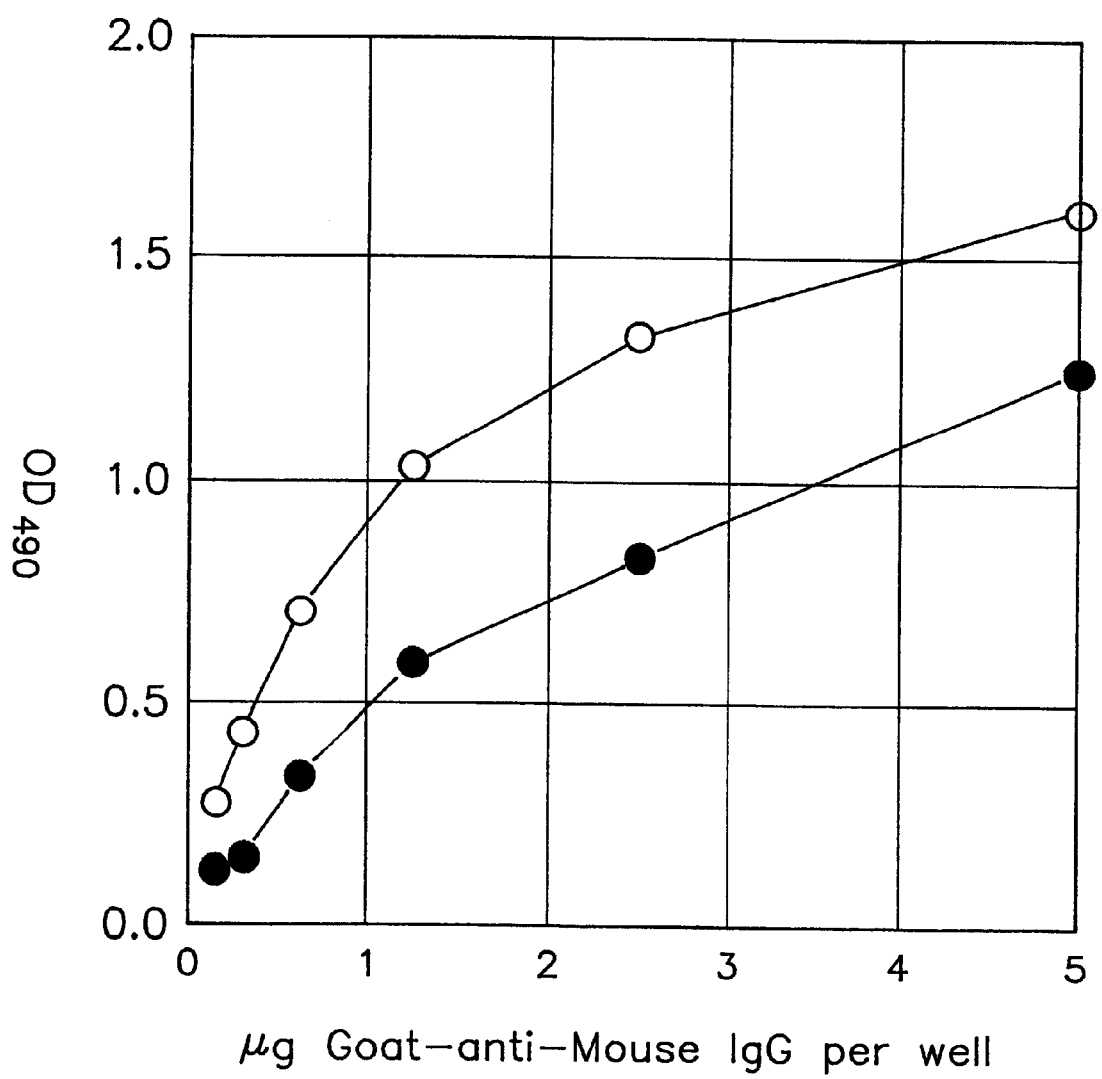
FIG. 6 shows the result of a sandwich-ELISA for detecting murine immunoglobulin, where the catching antibody (goat anti-mouse immunoglobulin) was immobilized to a POD-treated surface (○) and an untreated micro-titre-plate surface (●), respectively. The capacity for binding the catching antibody was examined by performing a titration thereof, and at the same time retaining the amount of the intermediate layer which contained murine IgG (Ox6).

It is seen from FIG. 6 that— in order to obtain a given signal—it is only necessary to add approx. ⅓ as much goat anti-mouse Ig on surfaces treated with POD as compared with untreated surfaces. This may either be due to the POD surface immoblilizing the catching antibodies (goat anti-mouse Ig) more efficiently, and/or the quality of the immobilized antibodies being better on these surfaces as compared with conventional passive adsorption.

Example 9

The influence of POD's oxidation degree for binding to the surface (a) Preparation of POD with Different Degree of Oxidation Six tubes containing dextran (100 mg, MW: 70,000) dissolved in 50 ml of distilled water were added with 0 mg, 132 mg, 263 mg, 398 mg, 530 mg, and 663 mg, respectively, of sodium periodate corresponding to a molar ratio between the OH-groups on dextran and periodate of 0, ½, 1, 1½, 2, 2½, respectively. After stirring for 2 hours dialysing was performed 3 times with 5 l pure water.

(b) Fixation of POD to Micro-titre-plates

To a micro-titre-plate (Maxisorp, Nunc) coated with poly-L-lysine as described in example 3, addition was made of 100 µl of POD (50 µg in PBS) having different degrees of oxidation. Hereafter incubation was for two hours, followed by wash 3 times with water.

(c) Immobilization of Biotin-MP7

100 µl of biotin-MP7 partly dissolved in PBS, and partly dissolved in carbonate buffer were added, whereafter incubation was performed for 2 hours, and wash three times with washing buffer.

(d) Detection of Biotin-MP7

This was detected as described in example 3.

Result and Discussion

Figure 7:
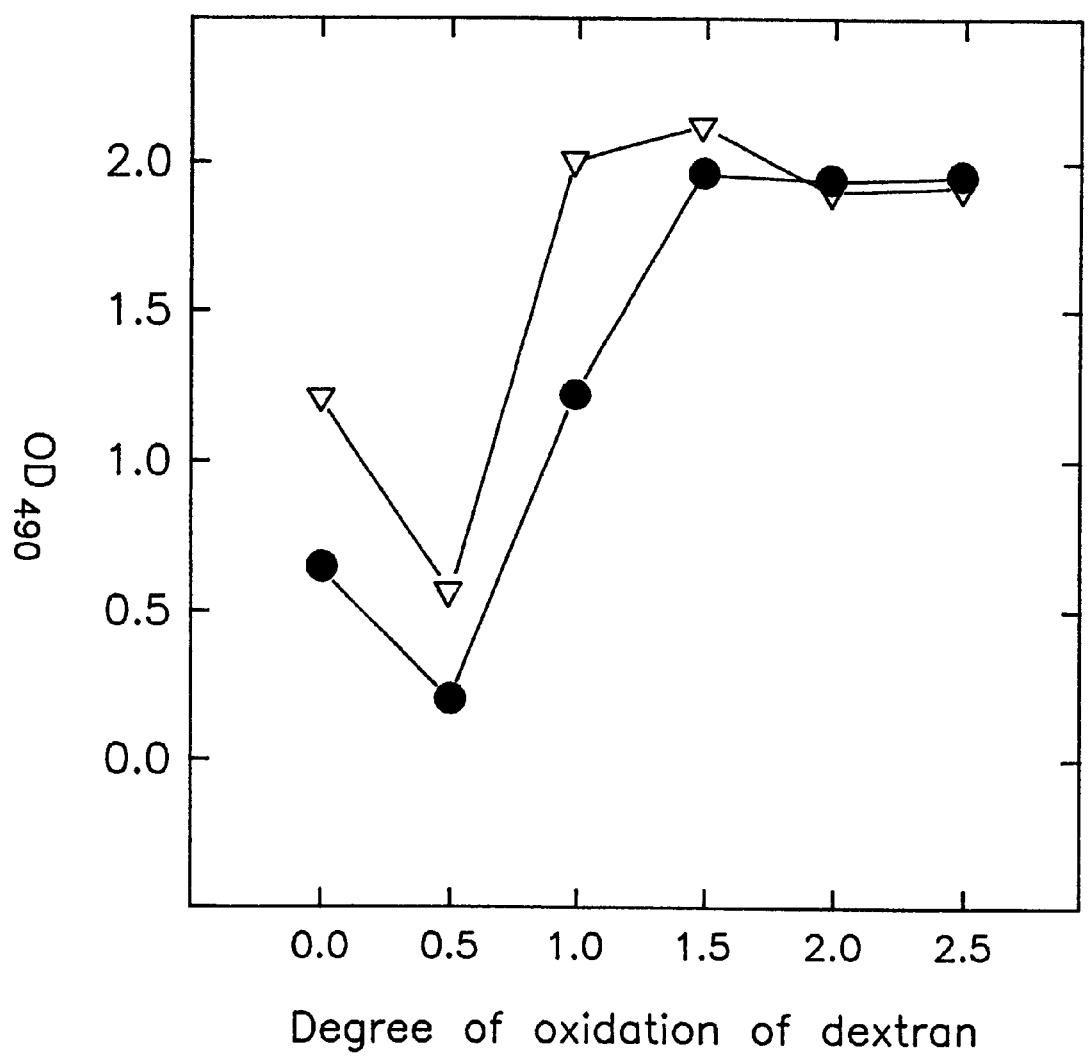
FIG. 7 shows the binding of biotin-MP7 to a POD-treated surface in PBS (▽) and in carbonate buffer (●), respectively. POD was oxidized to various degrees (0, ½, 1½, 2 and 2½). Hereby is meant that the molar ratio between the OH-groups on dextran and periodate during the oxidation was 0, ½, 1½, 2 and 2½, respectively.

An increase in the binding of MP7 was seen from where use was made of from 132 mg of perjodate to 398 mg of periodate per 50 mg of dextran, corresponding to a molar ratio between OH-groups in dextran and periodate of ½ to 1½. Hereafter no increase was seen (FIG. 7). This of course is because that at a molar ratio around 1 there are no more OH-groups which can be oxidized. In case of dextran without periodate a binding of 0.7 and 1.4 was seen in carbonate buffer and PBS, respectively. This is due to unspecific ionic interaction between biotin-MP7 and the poly-L-lysine layer. By addition of POD with low oxidation degree this binding becomes lower, since the majority of aldehyde- and ketone-groups on the dextran is now used for immobilizing POD to the surface, and thereby blocks biotin-MP7's access to poly-L-lysine. In case of a higher degree of oxidation of dextran, more and more free aldehyde- and ketone-groups will become capable of binding biotin-MP7 to the surface. At a degree of oxidation of more than 1½, POD therefore acts as a kind of fluid "double adhering tape" which partly binds the dextran to poly-L-lysine, and partly binds to biotin-MP7. This seems to function somewhat better in PBS (FIG. 7).

Example 10

The influence of POD's MW for binding to the surface (a) Preparation of periodate-activated dextran (POD) with different MW Three tubes with 100 mg of dextran (with a MW of 10,000, 70,000 and 2,000,000, respectively) were dissolved in 50 ml of distilled water, whereafter 398 mg of sodium perjodate was added to each tube. After stirring for 2 hours dialysing was performed 3 times with 5 l pure water.

(b) Fixation of POD to micro-titre-plates

To a micro-titre-plate (Maxisorp, Nunc) coated with poly-L-lysine as described in example 3, addition was made of 100 µl of POD (50 µg in 100 µl PBS, 0.1 M) from dextran with differing MW. After 2 hours the wells were washed three times with water.

(c) Immobilization of biotinylated MP7

Now addition was made of 100 µl of biotin-MP7 (1 µg/ml) diluted either in PBS or in carbonate buffer. After 2 hours the wells were emptied by suction, and washed three times with washing buffer.

(d) Detection of immobilized biotin-MP7

This was detected as described in example 1.

Result and Discussion

Figure 8:
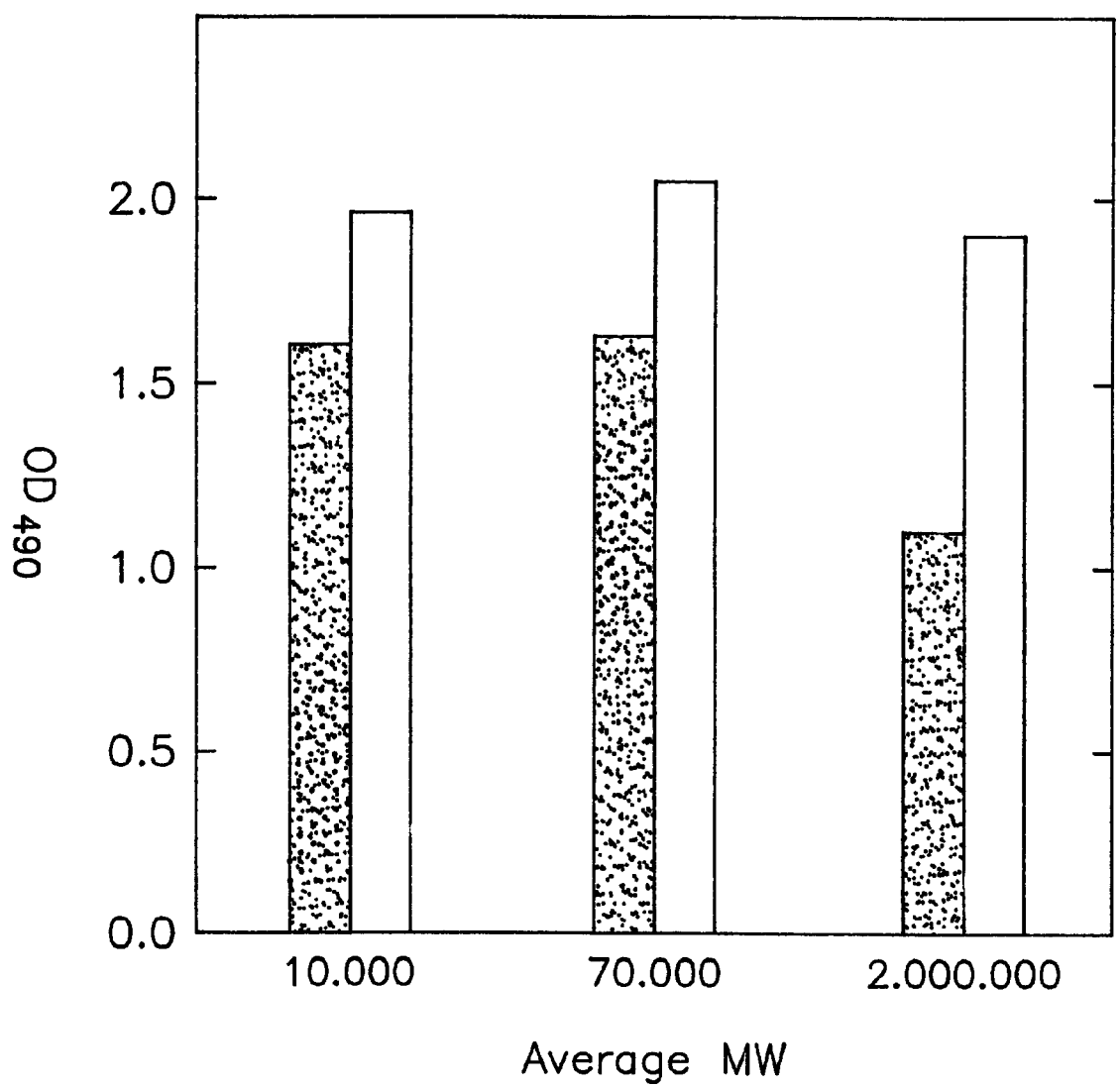
FIG. 8 shows the binding of biotin-MP7 to a POD-treated surface in carbonate buffer (■) and in PBS (□), respectively. The dextrans, which were used for producing POD, had a MW of 10,000, 70,000 and 2000,000, respectively.

Binding of biotin-MP7 was at the same level irrespective of MW of POD, except when biotin-MP7 was immobilized in carbonate buffer on POD from dextran with MW 2,000,000 (FIG. 8). Here a deterioration of the binding was seen. This could maybe be due to sterical hindrances. Dextran with MW 70,000 is thus satisfactory for most purposes. If dextran with a MW>1,000,000 is used, POD can to some extent be bound to the micro-titre-plate without this plate needing to be treated with e.g. poly-L-lysine (data not shown). POD with lower MW, however, does not bind to surfaces which do not contain primary amines.

Example 11

How much POD should be used in order to block a poly-L-lysine treated surface

Micro-titre-plates with poly-L-lysine were produced as described in example 3.

(a) Fixation of POD to micro-titre-plates

To the micro-titre-plate addition was made of 200 µl of POD (50 µg in 100 µl of PBS 0.1 M) with a MW of 10,000, 70,000 and 2,000,000, respectively. To the remaining wells was only added 100 µl of PBS, whereafter a 2fold titration was prepared. After 2 hours wash was performed three times with water.

(b) Binding of biotin-N-hydroxy succinimide ester (biotin-NHS-ester) to unblocked amino groups To each well was added 100 µl of biotin-NHS-ester (10 µg in PBS, Sigma), followed by incubation for 2 hours. Thereafter wash was performed 3 times with washing buffer.

(c) Detection of biotin

The amount of immobilized biotin was detected as described in example 3.

Result and Discussion

Figure 9:
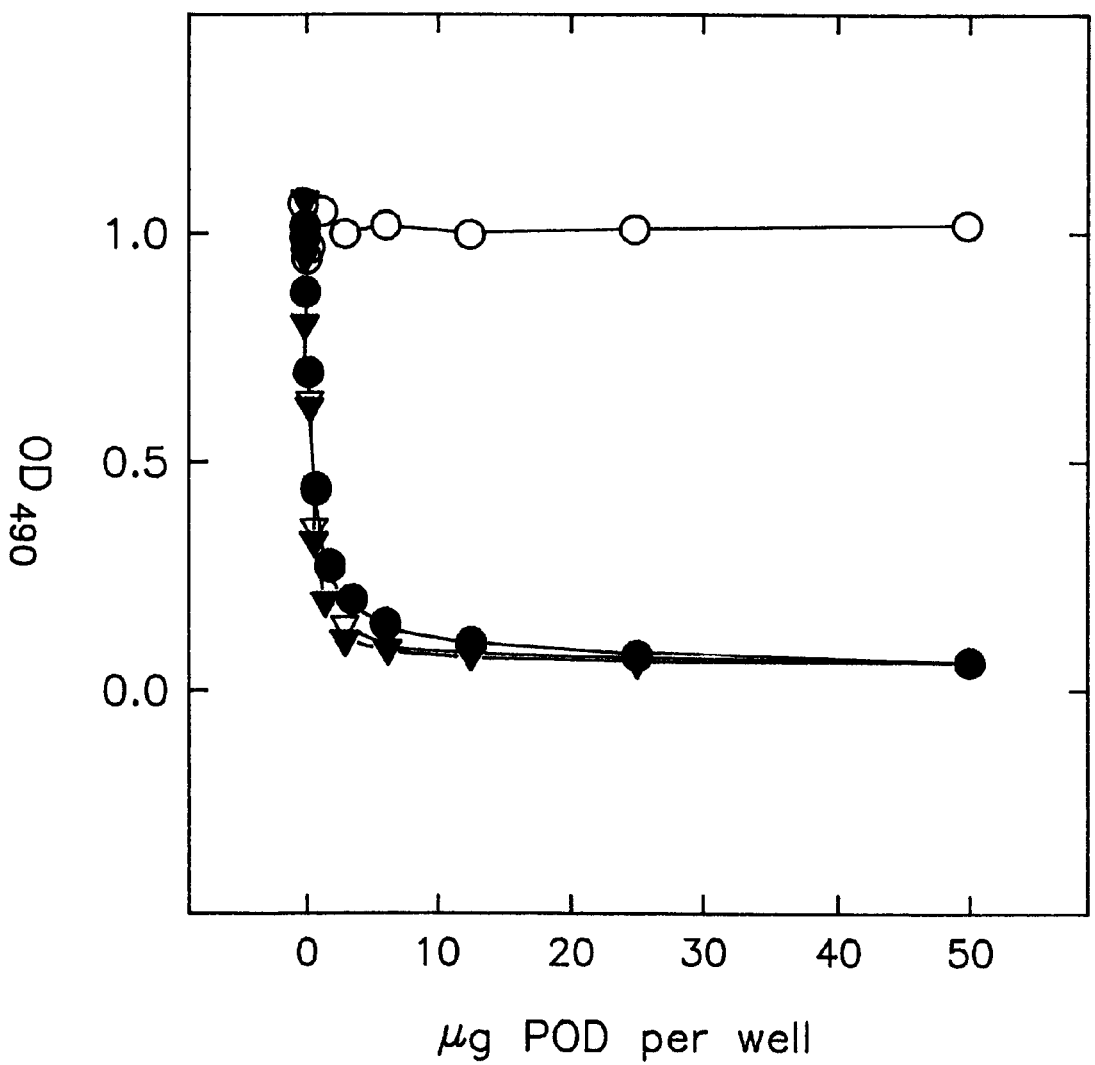
FIG. 9 shows binding of biotin-N-hydroxy succinimide to a poly-L-lysine coated surface, which was not treated (○) and treated, respectively, with different amounts of POD having MW of 10,000 (●), 70,000 (▽) and 2,000,000 (▼), respectively.

From FIG. 9 it appears that by using less than 5 μg of POD per well—irrespective of POD's MW—a strong increase was seen in the detection of biotin on the surface. This is an additional evidence that the observed binding to POD is specific and is not due to unspecific binding to poly-L-lysine. This layer is -thus efficiently shielded by POD.

Example 12

$NaBH_4$ provides non-binder properties

POD treated micro-titre-plates were produced as described in example 3.

(a) Addition of $NaBH_4$

To well 1A and 1B was added 200 μl of $NaBH_4$ (10 mg/ml in distilled water), whereafter a 2fold titration in water was produced. After 2 hours wash was performed 3 times with water.

(b) Preparation and addition of biotin-labeled BSA

Biotin-NHS-ester was dissolved in DMF (1.7 mg/ml, 5 μmol/ml), and BSA was dissolved in PBS (0.1 M, pH 7.2, 5 mg/ml). Hereafter 45 μl of biotin-NHS-ester solution was added to 1 ml of BSA solution. After 12 hours the mixture was diluted in PBS to 100 μg BSA/ml. After this incubation period all free biotin-NHS-ester had been hydrolyzed. To all wells in both rows was added 100 μl of the solution, and incubation was for 1 hour at room temperature.

(c) Detection of biotinylated BSA

The amount of immobilized biotinylated BSA was detected as described in example 3.

Result and Discussion

Figure 10:
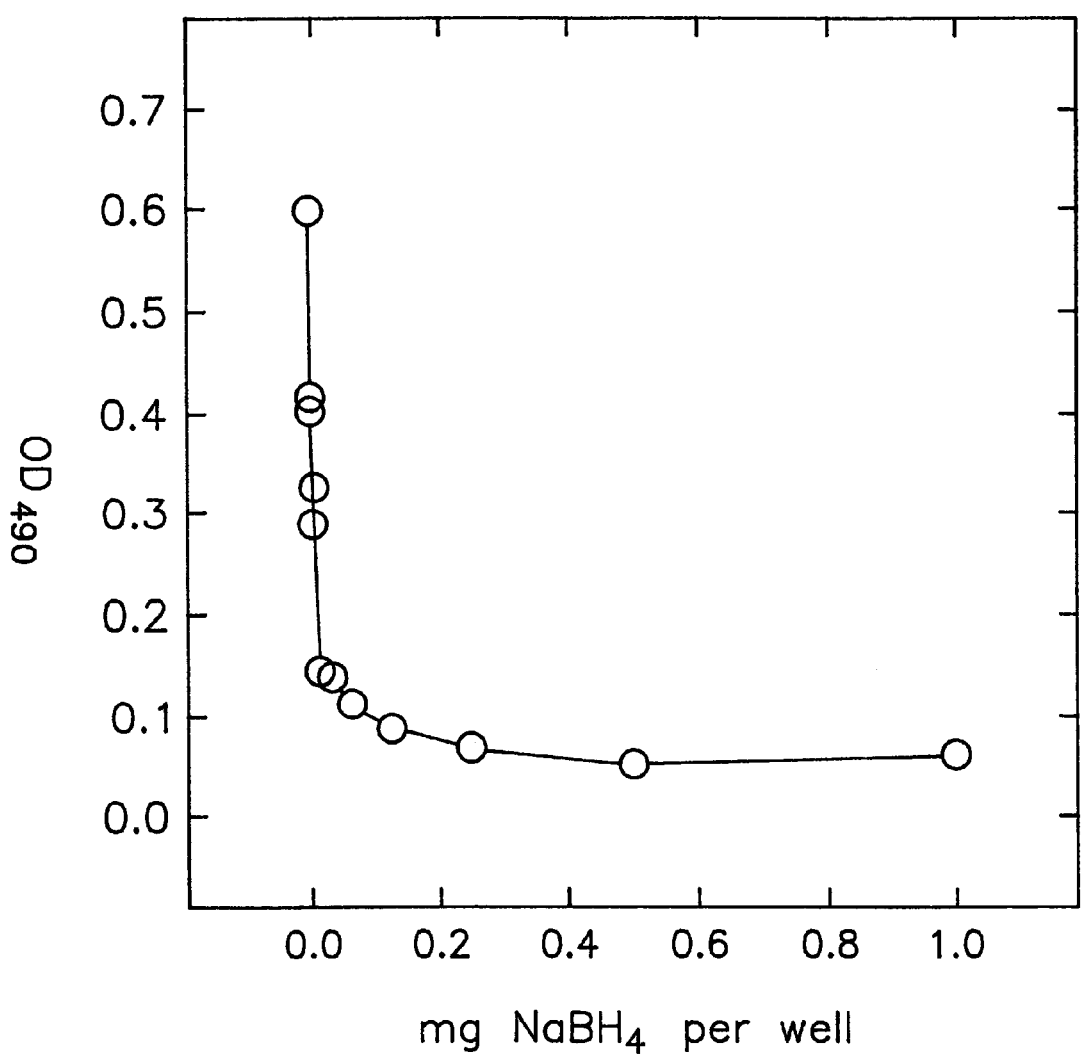
FIG. 10 shows binding of biotin-conjugated bovine serum albumin to POD-treated surfaces which in advance had been reduced with varying concentrations of $NaBH_4$.

It is seen from FIG. 10 that by using more than 0.2 mg of $NaBH_4$ per well the binding of BSA was hindered maximally. $NaBH_4$ is known to be able to reduce aldehydes and ketones to alcohols. Hereby the POD-surface will contain numerous hydrophilic OH-groups, which provides non-binder properties. The imines which were formed after the reaction between aldehyde-/ketone- and primary amino-groups are simultaneously reduced to secondary amines, whereby the binding between dextran and the primary amino groups on poly-L-lysine becomes irreversible.

Example 13

The stability of the POD surface

POD treated micro-titre-plates were produced as described in example 3.

(a) Addition of acid and bases, etc. to the POD surface

Addition was made of 100 μl of 0.1 N NaOH, 1 N NaOH, 0.1 N HCl, 1 N HCl, PBS pH 7.2, carbonate buffer pH 9.6, washing buffer and water, respectively, to the wells. These were hereafter left to stand for 1 hour at room temperature, followed by wash 3 times with water.

(b) Binding of biotin-NHS ester to unblocked amino groups

This was made as described in example 11.

(c) Detection of immobilized biotin

Procedure as described in example 3.

Result and Discussion

Figure 11:
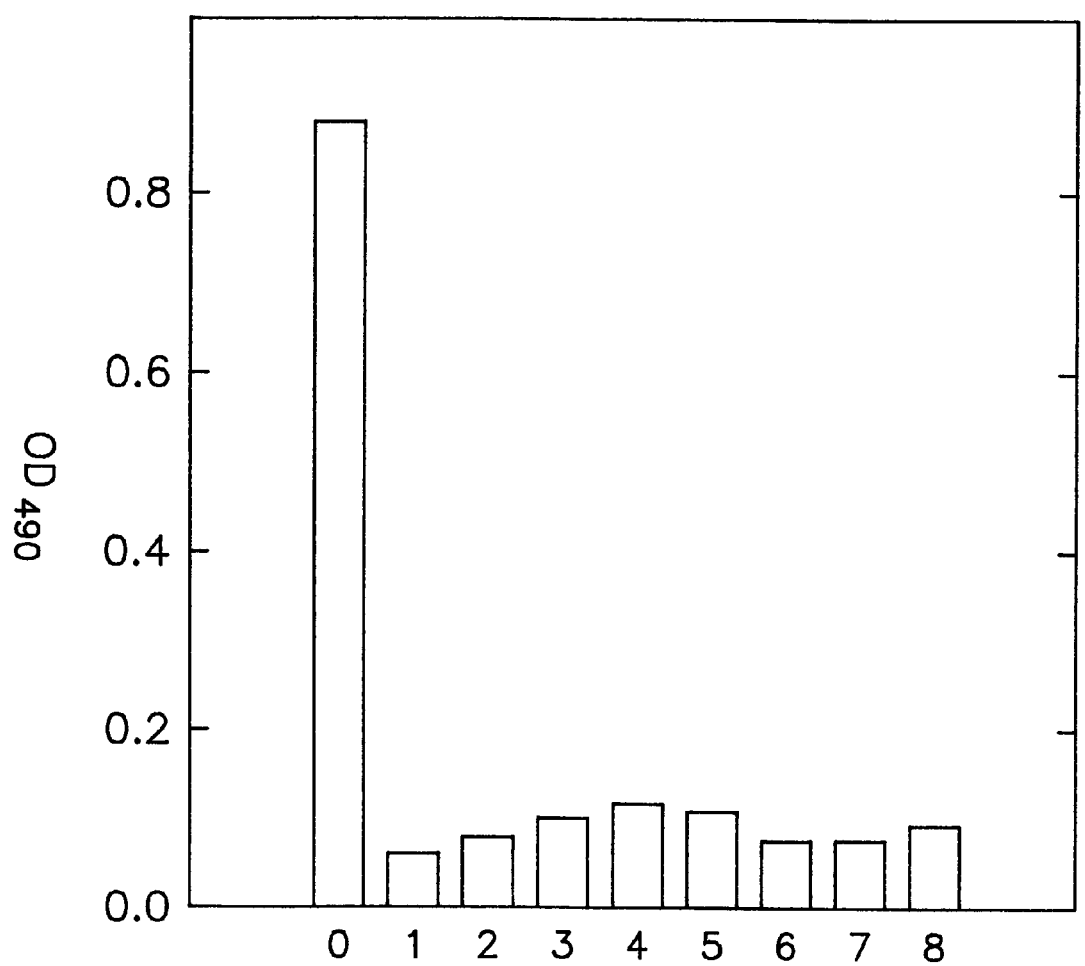
FIG. 11 shows binding of biotin-N-hydroxy succinimide to a poly-L-lysine coated surface which, respectively, was not treated with POD (0), and to surfaces which were treated with POD 70 000, and thereafter treated with 0.1 M NaOH (1); 1 M NaOH (2); 0.1 M HCl (3); 1 M HCl (4); PBS, pH 7.2 (5); 0.1 M carbonate buffer, pH 9.6 (6); washing buffer, pH 7.2 (7) and water (8), respectively, and FIGS. 12A and B show a durability comparison between goat-anti-mouse immobilized on micro-titre-plates with POD and without POD, respectively.
Figure 12A:
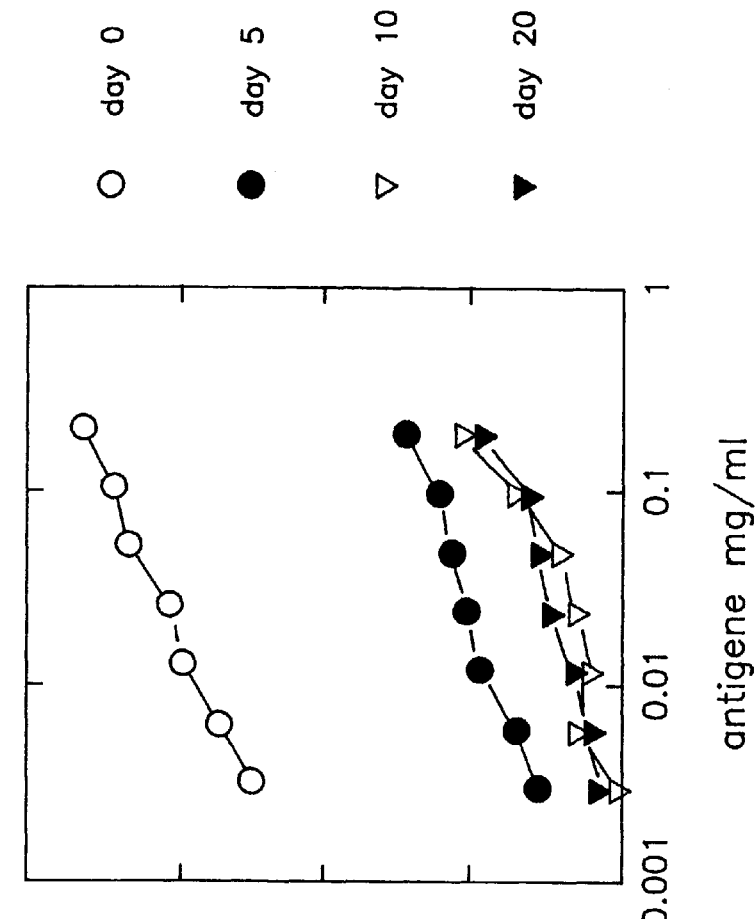
Figure 12B:
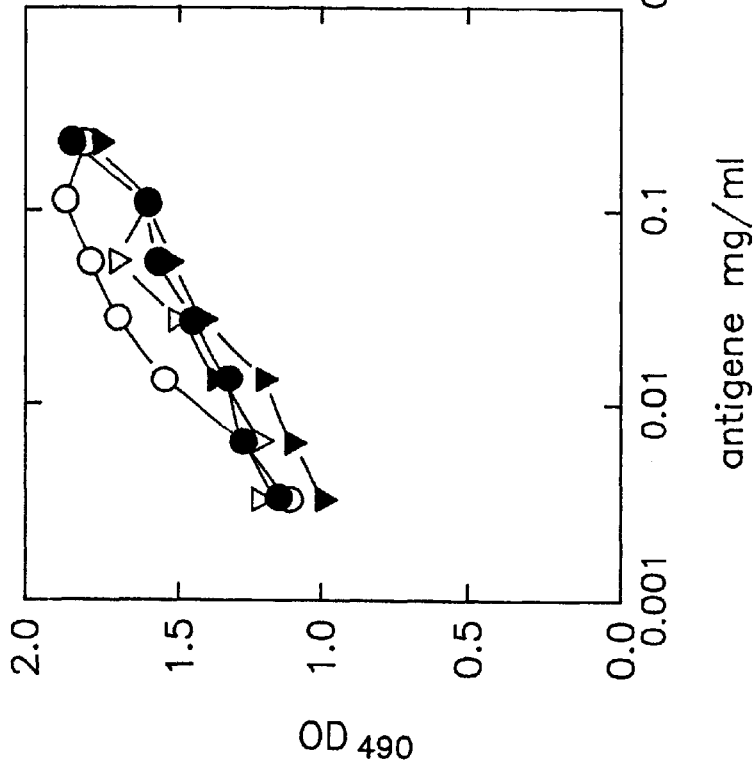

It is seen from FIG. 11 that the amount of amino groups detectable on the surface with biotin-NHS-ester after treatment with various strong acids and bases for comparison with the amount after treatment with water is unchanged low. If POD was not present, a strong binding was seen of biotin-NHS-ester to the primary amino groups of the poly-L-lysine layer. This means that POD is still present on the surface and thus cannot be removed by the above treatments. Thus the POD surface is particularly stable. In other (not shown) experiments we have also investigated the durability of the POD surfaces in PBS at different temperatures. This has been found to be unchanged fine within the entire test period which lasted for several weeks.

Example 14

Investigation of whether sera from normal human blood-donors react unspecifically with blocked POD-surfaces (a) Fixation of POD to micro-titre-plates POD treated micro-titre-plates were produced as described in example 1 and then blocked for 1 hour with 200 μl of 1% BSA in PBS added with 15% PEG 4000. The wells A–B, 1–3, were, however, instead added with 10 g/ml of affinity purified human IgG in PBS added with 15% PEG. Corresponding BSA and IgG treated plates were produced from ordinary (non-POD) treated micro-titre-plates. For the coating of the latter use was, however, not made of PEG. The plates were then washed 3 times with washing buffer.

(b) Addition of normal donor sera 60 sera from healthy blood donors of both sexes were diluted 1:100 in dilution buffer (washing buffer added with 1% BSA) and added to POD treated and untreated, respectively, micro-titre-plates. This was made in triplicate except to the wells A–C, 1–3. After incubation for 1 hour at room temperature, wash was performed 3 times with washing buffer.

(c) Detection of any Immobilized Human IgG

To all wells addition was then made of 100 μl of rabbit anti-human IgG (DAKO) diluted 1:1000 in dilution buffer, and incubation was for 1 hour at room temperature. Thereafter wash was performed 3 times with washing buffer. Immobilized peroxidase was then detected as described in example 3.

Result and Discussion

In wells to which human IgG had been added, average OD values of 2.1 and 1.8 were measured for POD-treated and untreated, respectively, micro-titre-plates. On both types of micro-titre-plates OD-values<0.05 were seen in the wells to which human sera (data not shown in figure form) had been added. POD treated plates thus exhibit comparable properties in relation to conventional untreated micro-titre-plates as regards unspecific binding.

Example 15

Durability of a catching antibody in a sandwich-ELISA

Catching antibody (0.002 mg/ml, 100 μl of goat-anti-mouse (TAGO) is immobilized to 4 micro-titre-plates without POD and 4 micro-titre-plates with POD, respectively, as described in example 8. For immobilization to the POD surfaces use is made of PEG. After immobilization the plates are washed with water and emptied and sealed with film and left to stand at 40 C.

After 0, 5, 10 and 20 days, respectively, a micro-titre-plates without POD and a micro-titration with POD are taken out. Hereafter 100 μl of antigene (monoclonal antibody from mice OX3 purified on a protein-A column from ascites) are added in 2fold titration, starting with a concentration of 0.2 mg/ml. After incubation for 1 hour at room temperature the plates are washed with washing buffer, and HPR labeled rabbit-anti-mouse (Dakopats A/S Denmark) is added in 1:1000, whereafter developing is as described in example 8.

Result and Discussion

It is seen from the figure that goat-anti-mouse immobilized on a micro-titre-plate with POD in a titration from 0.2 mg/ml to 0.0016 mg/ml results in an OD between 1.0 and 1.8, both on day 0, 5, 10 and 20.

On a micro-titre-plate without POD in a titration in the interval from 0.2 mg/ml to 0.0016 mg/ml is achieved an OD between 1.0 and 1.8 on day 0. On day 5 is seen in the same titration an OD between 0.6 and 0.2. On day 10 and 20 is seen an OD between 0.5 and 0.1.

From this it can be concluded that the durability of the catching-antibody on a micro-titre-plate with POD is the same on day 0, 5, 10 and 20, as opposed to the durability on a micro-titre-plate without POD, where the capacity of the catching antibody to bind antigene already on day 5 has fallen by 80%, and after day 10 is only with difficulty capable of binding antigene in high concentrations.

Similar experiments have shown that the durability of catching antibody on the POD surface is unchanged for at least 90 days.

What is claimed is:

1. An article selected from the group consisting of a microtiter plate, a microtiter strip, a particle, a membrane, a test tube, a test strip, and a measuring pin, said article comprising a water solubles tresyl-activated dextran which is fixed covalently to its surface.

2. An article selected from the group consisting of a microtiter plate, a microtiter strip, a particle, a membrane, a test tube, a test strip, and a measuring pin, said article comprising a water-soluble tresyl-activated, dextran fixated to the surface of the article.

* * * * *

UNITED STATES PATENT AND TRADEMARK OFFICE
CERTIFICATE OF CORRECTION

PATENT NO. : 6,262,256 B1
DATED : July 17, 2001
INVENTOR(S) : Elsner et al.

It is certified that error appears in the above-identified patent and that said Letters Patent is hereby corrected as shown below:

<u>Title page, Item [54] and Column 1, line 1,</u>
Correct the Title by replacing "TUESYL-ACTIVATED" with -- TRESYL-ACTIVATED --.
Item [75], Inventors: add the third inventor by inserting -- Klaus Gregorius, Brøinshøj, Denmark --.

Signed and Sealed this

Fifth Day of November, 2002

Attest:

Attesting Officer

JAMES E. ROGAN
*Director of the United States Patent and Trademark Office*